United States Patent [19]

Meyers et al.

[11] 3,953,494

[45] Apr. 27, 1976

[54] REACTIONS INVOLVING CARBON TETRAHALIDES AND α-METHYL KETONES OR KETONES HAVING α,α'-HYDROGENS

[75] Inventors: Cal Yale Meyers; Walter Sidney Matthews, III, both of Carbondale, Ill.

[73] Assignee: Southern Illinois University Foundation, Carbondale, Ill.

[22] Filed: Dec. 14, 1970

[21] Appl. No.: 98,078

[52] U.S. Cl. ........................ 260/468 R; 260/413; 260/410.9 R; 260/465.4; 260/468 G; 260/470; 260/473 G; 260/476 R; 260/478; 260/481 R; 260/482 R; 260/484 R; 260/486 D; 260/488 F; 260/514 R; 260/514 G; 260/515 R; 260/516; 260/520 R; 260/526 R; 260/526 N; 260/526 S; 260/534 R; 260/535 R; 260/540; 260/586 P; 260/590 D; 260/591; 260/592; 260/593 R; 260/593 H; 260/598; 260/599; 260/600 R; 260/601 R; 260/590 R

[51] Int. Cl.².................. C07C 51/28; C07C 67/42

[58] Field of Search ............ 260/540, 514 R, 526 R, 260/526 N, 526 S, 488 F, 468 R, 413, 410.9 R, 478, 515 R, 476 R, 486 D, 535 R, 534 R, 520, 516, 470, 481 R, 482 R, 484 R, 473 G, 465.4

[56] References Cited

OTHER PUBLICATIONS

Organic Reactions, Vol. 13, 1963, pp. 58–64.

*Primary Examiner*—Vivian Garner
*Attorney, Agent, or Firm*—Koenig, Senniger, Powers and Leavitt

[57] ABSTRACT

A process for preparing aldehydes, ketones, carboxylic acids and esters by reaction of various substrates with carbon tetrahalides in the presence of a strong base. The reactions are accelerated by the presence of a polar solvent. Anions of the substrate attack the carbon tetrahalide to produce a halogenated intermediate and a dihalocarbene. The halogenated intermediate reacts with the base to form the indicated products. By the reactions of this process, primary alcohols are converted to aldehydes, carboxylic acids and esters, secondary alcohols are converted to ketones and ketones having an α-methyl group or both α and α' hydrogens are converted to carboxylic acids and esters. Non α-methyl ketones having α but no α' hydrogens are simply α-halogenated. The dihalocarbene generated in the reaction may attack the product, solvent, or another substrate to form other products.

24 Claims, No Drawings

REACTIONS INVOLVING CARBON TETRAHALIDES AND α-METHYL KETONES OR KETONES HAVING α,α'-HYDROGENS

BACKGROUND OF THE INVENTION

This invention relates to the field of organic chemistry and more particularly to ionic reactions of certain carbon tetrahalides with various organic compounds.

Carbon tetrachloride is generally considered to be a compound of limited chemical reactivity and has found application in a number of services which capitalize on its relative chemical inertness. Thus, for example, carbon tetrachloride is useful as a fire extinguishing agent, as a cleaning solvent and as a solvent for organic chemical reactions. For many years carbon tetrachloride found its principal application as a solvent, particularly for cleaning purposes. Recently, this market has been substantially closed off, however, due to government restrictions relating to the toxicity of carbon tetrachloride.

The use of carbon tetrachloride as a chemical intermediate has heretofore been restricted to a few specialized reactions. Commercial production of chloroform, for example, is carried out by reduction of carbon tetrachloride with iron and water. Compounds marketed under the trade designation "Freons" such as dichlorodifluoromethane and trichloromonofluoromethane are produced commercially by partially displacing chlorine from carbon tetrachloride with fluorine. The production of such "Freon" compounds has represented the principal commercial outlet for carbon tetrachloride for several years, and in recent years has provided the only major market for this material.

In 1876, Reimer and Tiemann discovered that phenol could be converted to ortho and parahydroxybenzaldehydes by reaction with chloroform in an aqueous alkaline medium. When they substituted carbon tetrachloride for chloroform, added ethanol and held the reaction mixture in a sealed tube at 100° C. for 3 days, a mixture of ortho and parahydroxy benzoic acid was produced. The work of Reimer and Tiemann with carbon tetrahalides was limited to the particular reaction noted above, i.e., the addition of a carboxylic acid group para or ortho to a phenolic hydroxy group, using an ethanolic aqueous alkaline medium.

Because of its abundance and relative inexpensiveness, carbon tetrachloride is potentially a very attractive chemical intermediate. Prior to the present invention, however, this compound was considered to be a substantially inert material whose chemical activity was limited to certain particular reactions such as those outlined above.

SUMMARY OF THE INVENTION

It is an object of the present invention to provide a method of producing useful compounds by reaction of various substrate materials with carbon tetrahalides such as carbon tetrachloride and carbon tetrabromide. Another object of this invention is to produce certain organic compounds in a more convenient and economical manner than has previously been practical. Other objects and features will be in part apparent and in part pointed out hereinafter.

Briefly, the present invention is directed to an improvement in a process for preparing aldehydes, carboxylic acids and esters from primary alcohols, for preparing ketones from secondary alcohols, and for preparing carboxylic acids and esters from α-methyl ketones or ketones having α and α' hydrogens. The improvement comprises initially reacting a substrate selected from the group consisting of primary alcohols, secondary alcohols, α-methyl ketones and ketones having α and α' hydrogens with a carbon tetrahalide represented by the formula $CBr_mCl_nF_p$ where $n$ and $m$ are integers between 0 and 4 inclusive, $p$ is an integer between 0 and 2 inclusive, $n+m+p=4$, in the presence of a strong base to form a halogenated intermediate and a dihalocarbene. The present invention is also directed to such a process wherein the halogenated intermediate thus produced reacts in situ with the base to form the product aldehyde, ketone, ester, or carboxylic acid. The invention is further directed to a process for preparing α-halogenated ketones having no α' hydrogens which comprises the steps of: reacting a ketone having no α' hydrogens and having either one or two α hydrogens with a carbon tetrahalide of the aforementioned type in the presence of a strong base to form an α-halogenated ketone product and a dihalocarbene.

DESCRIPTION OF THE PREFERRED EMBODIMENTS

In accordance with the present invention, numerous partially oxidized organic substrates may be reacted with certain carbon tetrahalides in the presence of strong bases such as alkali metal hydroxides or metal alkoxides to effect further oxidation and produce a number of useful products. In the presence of such a strong base, normally unreactive carbon tetrahalides such as carbon tetrachloride and carbon tetrabromide can be made to react with a wide variety of such substrates as primary alcohols, secondary alcohols, and ketones. Thus primary alcohols can generally be converted to aldehydes, carboxylic acids and carboxylic esters, secondary alcohols to ketones, and ketones to carboxylic acids. These reactions, it has been discovered, proceed rapidly at moderate temperatures, e.g., room temperature or lower up to the reflux temperature of the system, and produce a wide range of products in good yield, certain of which are impractical or uneconomical to produce according to previously known methods.

While we do not wish to be held to any particular theory, it is postulated that the reactions involved in the process of the present invention proceed according to the following equations (where $CCl_4$ is shown as illustrative of the useful tetrahalides):

$$Nu\text{-}H \rightleftarrows Nu\text{:}^- + ROH \qquad (1)$$

$$Nu\text{:}^- + ClCCl_3 \rightarrow NuCl + \text{:}CCl_3^- \rightleftarrows \text{:}CCl_2 + Cl^- \qquad (2)$$

$$NuCl \xrightarrow[CCl_4]{OR^-} products \qquad (3)$$

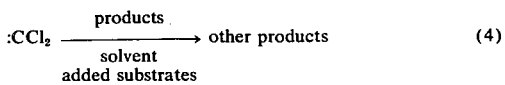

$$\text{:}CCl_2 \xrightarrow[\substack{solvent \\ added\ substrates}]{products} other\ products \qquad (4)$$

In reaction (1) the substrate material NuH reacts with the strong base yielding a nucleophilic anion Nu:⁻. This anion in turn attacks one of the halogen atoms of the carbon tetrahalide [equation (2)], yielding a halogenated intermediate and a trihalomethyl anion which dissociates into a dihalocarbene and a halide ion. The halogenated intermediate may undergo further halogenation or react with the base to form products as in equation (3). Depending upon the nature of the substrate, the dihalocarbene may react with the substrate products or solvent or added substrates to form other products, as indicated in equation (4). The halogenated product formed according to equation (4) may also react with the base as in equation (3) to form other products.

Once monohalogenation has taken place as in equation (2), multiple halogenation at that position proceeds even more rapidly. Where the nature of the substrate permits intramolecular reaction of the monohalogenated species by means of the base, however, the latter reaction takes place much more rapidly than multiple halogenation, and the corresponding oxidation products are preferentially produced. Thus, a novel route is provided to certain oxygenated hydrocarbons, with the monohalogenation step indicated in equation (2) being the rate controlling step.

Under conditions wherein the strong base remains a solid during the reaction, the halide ion produced in equation (2) forms the halide salt of the metal of the strong base and precipitates. This halide salt often tends to collect at and coat the surface of the strong base, thus impeding the formation of the Nu:⁻ anion per equation (1) and the formation of products per equation (3). The rates and yields of the reactions of the invention, particularly those where the kinetics of the anion formation are relatively slow, may be adversely affected by this phenomenon. It is preferred, therefore, that a small quantity of water be present in the reaction medium, especially in those reactions where anion formation is slow. In such instances, the presence of an amount of water on the order of one mole per mole of substrate dissolves the halide salt as it is formed and prevents the interference of the salt with the formation of either the carbanion or the products.

The reactions of this invention are accelerated if a solvent for the substrate and the carbon tetrahalide is incorporated in the reaction system. Where the substrate is an alcohol, no particular advantage normally accrues from the use of a separate solvent. Where the substrate is a ketone, however, the use of a solvent such as, e.g., an alcohol, polyol, cyclic ether, aliphatic ether, cyclic polyether, aliphatic polyether, tetrahydrofuran, glyme, diglyme, liquid ammonia, or liquid sulfur dioxide is preferred. t-Butyl alcohol has been found to be a particularly useful solvent, since it does not react with the substrate and has sufficient volatility to be readily stripped off during product recovery.

The preferred carbon tetrahalide reactant is carbon tetrachloride. However, $CBr_4$ will also perform satisfactorily in these reactions, as will $CBrCl_3$, $CBr_2Cl_2$, $CBr_3Cl$, $CCl_3F$, $CCl_2BrF$, $CClBr_2F$, $CBr_3F$, $CCl_2F_2$, $CClBrF_2$ and $CBr_2F_2$. Generally, therefore, any compounds having the formula $CBr_mCl_nF_p$ where m and n are integers between 0 and 4 inclusive, p is an integer between 0 and 2 inclusive, and m+n+p = 4 can be utilized as the tetrahalide reactant in this invention.

The strong base used in this invention is preferably an alkaline hydroxide, e.g., NaOH or KOH, where the product sought is an aldehyde, ketone or acid. Esters are produced using a metal alkoxide such as a sodium, potassium or aluminum alkoxide.

Where the substrate material is a primary alcohol, the reaction is thought to proceed according to the following sequence (with $CBr_4$ being shown as an illustrative tetrahalide):

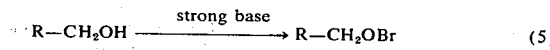

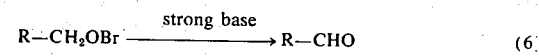

where R is hydrogen or a substituted or unsubstituted alkyl, aryl, aralkyl, alkenyl, alkynyl, aralkenyl, aralkynyl, cycloalkyl or cycloalkenyl group. Thus, essentially any primary alcohol may be converted to its corresponding aldehyde in accordance with the processes of this invention. Illustrative primary alcohols which may be so converted include:

propanol
allyl alcohol
ethylene glycol
propylene glycol
cyclohexanol
butanol
benzyl alcohol
cinnamyl alcohol
propargyl alcohol
phenyl propargyl alcohol
cyclohexenyl carbinol
1-naphthyl carbinol
2-naphthyl carbinol
1-hexyn-6-ol
isobutyl alcohol
neopentyl alcohol
saligenin
4-hydroxybenzyl alcohol
2-pentene-5-ol
cyclopentyl carbinol It should be noted that the conversion of o-hydroxybenzyl alcohol to its corresponding aldehyde (salicylaldehyde) by carbon tetrahalide is quite remarkable, since other halogenating agents generally attack the ring.

The aldehyde formed in equation (6) may subsequently undergo aldol condensations leading to polymers or undergo the Cannizzaro reaction leading entirely to carboxylic acids or esters. Thus, for example, a mole of benzaldehyde produced from benzyl alcohol disproportionates in the presence of an alkali hydroxide or alkoxide to half a mole of benzoic acid or alkyl benzoate ester and half a mole of benzyl alcohol. The benzyl alcohol thereby regenerated undergoes oxidation according to the reactions of this invention to form additional benzaldehyde which again disproportionates into alcohol and acid or ester, and so on until all of the material is converted to benzoic acid or alkyl benzoate ester. There are certain alkali resistant aldehydes, such as salicylaldehyde produced from ortho hydroxy benzyl alcohol and pivalaldehyde from neopentyl alcohol, which cannot undergo the aldol condensation and are substantially resistant to the Cannizzaro reaction, and can, therefore, be isolated as such from the reaction medium.

By a mechanism similar to that set forth in equations (5) and (6), secondary alcohols are converted to the corresponding ketones.

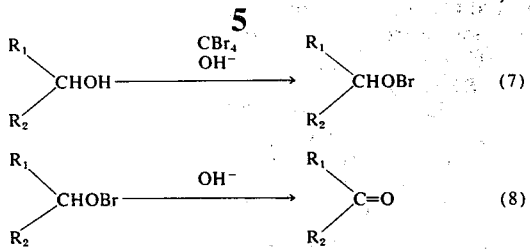

(7)

(8)

where $R_1$ and $R_2$ are a substituted or unsubstituted alkyl, aryl, aralkyl, alkenyl, aralkenyl, alkynyl, aralkynyl, cycloalkyl or cycloalkenyl group. Similarly, secondary alcohols of the formula $R_3OH$ where $R_3$ is cycloalkyl or cycloalkenyl are converted to ketones of the formula $R_4O$ where $R_4$ is cycloalkylidenyl or cycloalkenylidenyl. Thus essentially any secondary alcohol may be converted to its corresponding ketone by the reactions of this invention. Among the various secondary alcohols which may be so converted are:

cyclooctanol
cyclohexanol
cinnamyl methyl carbinol
dibenzyl alcohol
benzhydrol
methyl isopropyl carbinol
benzhydryl methyl carbinol
sec butyl alcohol
cyclohexyl methyl carbinol
3-hydroxy-cyclohexene
benzyl methyl carbinol
diallyl carbinol
styryl methyl carbinol
2-methyl cyclopentanol However, when the ketones produced contain $\alpha$ hydrogens, subsequent reactions occur. Where the ketone produced by oxidation of a secondary alcohol possesses $\alpha$ and $\alpha'$ hydrogens, it is further converted to carboxylic acids or esters in accordance with the ketone reaction scheme set forth infra. For example, 1-methyl 2,2-diphenyl ethanol is converted to $\beta,\beta$-diphenylpropionic acid via methyl benzyl ketone while 1,3-dimethyl butanol is converted to pivalic acid via methyl isopropyl ketone. If the ketone produced has $\alpha$ but not $\alpha'$ hydrogens, $\alpha$-halogenation occurs. When $\alpha$-trihalogenation occurs, the final product is usually the carboxylic acid in accordance with the ketone reaction scheme set forth infra. If the ketone produced contains neither $\alpha$ nor $\alpha'$ hydrogens, it may be isolated from the reaction mixture. Thus benzophenone is recovered from the reaction mixture where the substrate used is benzhydrol.

In accordance with the reaction scheme of this invention, the strong base associates with ketones having $\alpha$ hydrogens and abstracts an $\alpha$ hydrogen as a proton from an $\alpha$ carbon. The resulting carbanion is then monohalogenated by the carbon tetrahalide. If the ketone substrate initially possesses both $\alpha$ and $\alpha'$ hydrogens, the monohalogenated species is converted to a carboxylic acid or ester via the Favorskii rearrangement. Thus, as shown below, the mono-$\alpha$-haloketone is converted to a cyclopropanone.

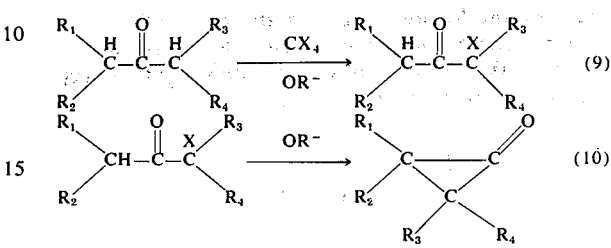

(9)

(10)

where $CX_4$ represents the carbon tetrahalide and where R is hydrogen or alkyl and $R_1$, $R_2$, $R_3$ and $R_4$ are hydrogen, alkoxy, aryloxy, alkylthio, arylthio, nitro, cyano, amino, substituted amino and substituted or unsubstituted alkyl, aryl, aralkyl, alkenyl, alkynyl, aralkenyl, aralkynyl, cycloalkyl or cycloalkenyl group. The cyclopropanone is in turn attacked by a hydroxyl ion at the carbonyl group, breaking the three-membered ring and yielding the carboxylic acid. The point of ring cleavage varies with the nature of substituents on the ring. For example, methyl isopropyl ketone is converted to a cyclopropanone which cleaves at the bond between the carbonyl group and the unsubstituted methyl group, producing pivalic acid or a corresponding ester:

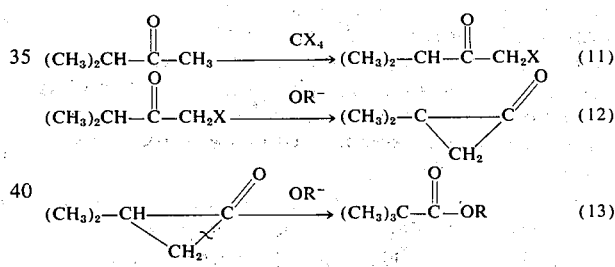

(11)

(12)

(13)

where R is hydrogen or alkyl.

On the other hand, 1,1-diphenyl acetone is converted to a cyclopropanone which cleaves at the bond between the carbonyl group and the diphenyl methyl group, yielding $\beta,\beta$-diphenylpropionic acid or corresponding ester:

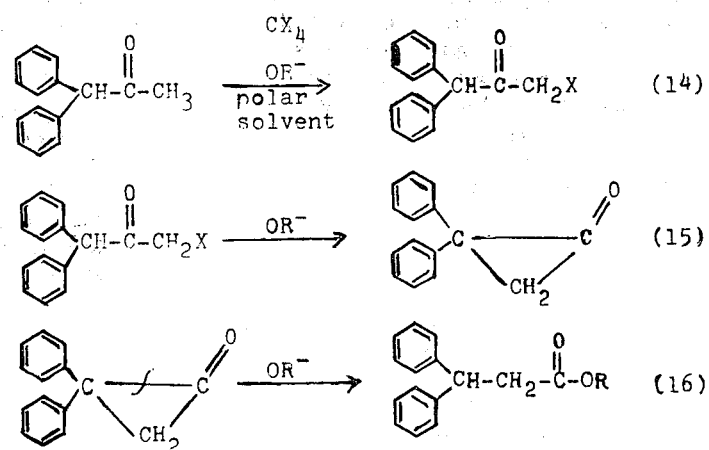

(14)

(15)

(16)

where R is hydrogen or alkyl, and $CX_4$ represents $CBr_mCl_nF_p$.

Cyclic and cyclic substituted ketones having both $\alpha$ and $\alpha'$ hydrogens are also converted to carboxylic acids or esters by the reactions of the invention. Cyclic substituted carboxylic acids and esters are obtained from substrates having the formula:

where at least one of X and Y is a cycloalkyl or cycloalkenyl group. The other of X and Y may also be alicyclic or may be a radical corresponding to the formula:

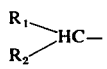

where $R_1$ and $R_2$ are as defined above.

Among the cyclic ketones which may serve as substrates for the reactions of the invention are those represented by the structural formula:

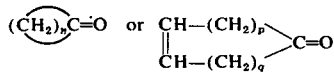

In these formulae n is an integer greater than or equal to 2 and p and q are integers. The methylene substituted derivatives of such ketones are also useful substrates.

Where the ketone substrate initially possesses $\alpha$ but no $\alpha'$ hydrogens, the monohalogenated ketone intermediate resulting from substitution of halogen for an $\alpha$ hydrogen is not subject to attack by the base present, and multiple halogenation ensues. Methyl ketones having no $\alpha'$ hydrogens are readily trihalogenated and the resultant trihalo ketone is subsequently converted to a carboxylic acid or ester via the haloform reaction. Thus, for example,

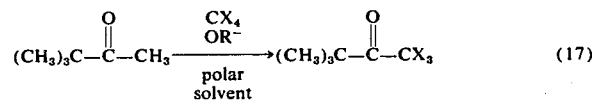

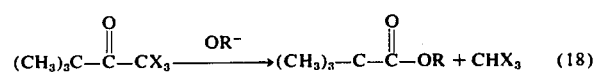

Essentially any methyl ketone, as well as essentially any ketone having both $\alpha$ and $\alpha'$ hydrogens is converted to its corresponding acid or ester by the reactions of this invention. Among the various ketones which are converted to acids or esters may be noted:
  diethyl ketone
  acetone
  methyl ethyl ketone
  dibenzyl ketone
  4-phenyl-2-butanone
  1-pentene-4-one
  1-pentyne-4-one
  1-phenyl-1-pentene-4-one
  1-phenyl-1-pentyne-4-one
  cyclohexyl acetone
  cyclohexenyl acetone
  ethyl cyclohexyl ketone
  isopropyl cyclopentyl ketone
  cyclohexanone
  3-ethyl cyclohexanone
  cycloheptanone
  cyclohexene-4-one
  1-methyl cyclohexene-4-one
  cycloheptene-4-one
  1,2-dimethyl cycloheptene-4-one Non-$\alpha$ methyl ketones having $\alpha$ but no $\alpha'$ hydrogens are halogenated by displacement of hydrogen by halogen at the $\alpha$ carbon atom and can be isolated from the reaction mixture, for example
  isobutyrophenone
  propiophenone
  t-butyl ethyl ketone
  t-butyl isopropyl ketone
  phenyl neopentyl ketone The above-listed ketones which have two $\alpha$ hydrogens are dihalogenated.

Where the substrate is of the type which may be converted to a carboxylic acid, esters are produced by using a metal alkoxide as the base in the reaction mixture. Thus, where the substrate material is methyl isopropyl ketone and the reaction mixture includes potassium tertiary butoxide, tertiary butyl pivalate is formed. Because of the highly hindered alcohol and acid moieties by which it is constituted, this ester is not formed by conventional esterification procedures. The processes of this invention provide uniquely advantageous routes to highly hindered esters of this type.

As indicated in equation (4), the dihalocarbene generated by the attack of the anion on carbon tetrahalide can react with substrate, solvent, or products to form other products. When phenol is present as a secondary substrate in the reaction system, dihalocarbene, generated by reaction of carbon tetrahalide with the primary substrate, substitutes on the phenolic ring leading to the formation of o- and p-hydroxybenzaldehyde. The latter products may be recovered from the reaction mixture since they do not undergo the aldol condensation and are resistant to the Cannizzaro reaction at the relatively mild conditions under which the reactions of this invention are normally conducted.

The reactions of this invention proceed rapidly in high yield at moderate temperatures. Temperatures from just above the solidification point of the reaction system up to a temperature of about 250°C. may be employed. Higher temperatures can be tolerated but are normally unnecessary. Conveniently the reactions are simply carried out at room temperature. To facilitate particularly rapid reactions and high conversion, the reaction system is maintained above atmospheric reflux temperature, for example 150°C.

The relative proportions of reactants are in no way critical, and may be varied widely. A substantial excess of carbon tetrahalide, base and polar solvent promotes rapid reaction and high conversions. Lower excesses, however, provide larger reactor payloads and, as will be appreciated by those skilled in the art, the optimum commercial reactant ratios depend on the substrates and products involved, the capacities desired, the separation processes selected, and whether batch or continuous operations are employed.

In the processes of this invention, the product may be recovered from the reaction mixture by any convenient means known to the art. Thus, various combinations of distillation, crystallization, filtration and extraction may be used. In one particularly convenient method of recovering an acidic product, water is added to the residue and the resultant mixture extracted with a first aliquot of an organic solvent such as ether. Prior to this first extraction, it may be convenient to strip off excess solvent, particularly where high relative proportions of carbon tetrahalide and polar solvent are used. An alkaline solution containing the bulk of the product is separated from the organic solvent extract. If the latter contains significant quantities of product, it should be washed with water and the washings mixed with the alkaline solution. The alkaline solution is then acidified and extracted with a second aliquot of an organic solvent. The second organic solvent extract, containing the product, is washed with water, dried, filtered and evaporated to recover the product. The first organic solvent extract, after washing, may also be dried and evaporated to recover unconverted substrate material.

When the major product is not acidic, the product will remain in the original organic solvent extract, from which it may be recovered. It is often advantageous not to add water to the reaction mixture prior to extraction, if the product is a carboxylic ester. In this way alkaline hydrolysis can be prevented and the ester product recovered satisfactorily.

As a result of the high rates and yields realized under mild conditions, and the low cost of reagents such as carbon tetrachloride, the reactions of this invention possess economic advantages over previously known methods of producing certain oxidized organic compounds. Particular advantages arise in the production of compounds such as pivalic acid and $\beta,\beta$-diphenyl propionic acid. Previously known routes to these acids have involved independent preparation of the $\alpha$-haloketone, followed by the Favorskii rearrangement. Since the $\alpha$-haloketones are severe lachrymators, obvious difficulties and expense arise in handling them. By the reactions of the instant invention, however, the haloketones are converted to the corresponding acids in situ as rapidly as they are formed, thus avoiding the inconvenience and expense associated with handling these physiologically obnoxious compounds.

Phenols are generally attacked at the ring by halogens, and are generally prone to attack by oxidizing agents. By the process of this invention, however, phenolic alcohols and ketones are transformed into aldehydes, esters, carboxylic acids, etc. without effecting alteration of the phenolic nucleus.

The following examples illustrate the invention:

EXAMPLE 1

1 g. of methyl isopropyl ketone was added to 15 ml. of $CCl_4$ and 5 g. solid potassium hydroxide and the mixture was refluxed for 14 hours. 100 ml. $H_2O$ was added and the resulting alkaline aqueous layer was separated from the $CCl_4$ layer. The alkaline aqueous layer was washed with ether 3 times (100 ml. portions). The extracted aqueous layer was acidified with concentrated HCl and extracted with ether. The ether phase was dried and the ether solvent removed under vacuum, yielding 0.4 g. of pivalic acid.

EXAMPLE 2

0.010 moles of 1,1-diphenyl acetone was dissolved in a mixture of 15 ml. of carbon tetrachloride and 5 ml. of tertiary butyl alcohol. 4 g. of powdered potassium hydroxide was added. The resultant mixture was stirred for 20 minutes under reflux. Water was then added to the reaction mixture and the aqueous phase was washed 3 times with separate half volume aliquots of ether. The extracted alkaline aqueous layer was acidified with concentrated hydrochloric acid and allowed to cool. A precipitate formed and the entire mixture was extracted with 3.5 ml. portions of ether. The resulting ether solution was then dried with anhydrous magnesium sulfate and the ether distilled off, leaving 1.60 g. of crude $\beta,\beta$-diphenyl propionic acid in the form of a yellow solid (melting point 148° to 151°C.). Recrystallization provided a colorless to milk-white solid having a melting point of 153° to 155°C.

EXAMPLE 3

0.010 moles of methyl isopropyl ketone was dissolved in a mixture of 15 ml. of carbon tetrachloride and 5 ml. of tertiary butyl alcohol. 2 ml. water and 4 g. of powdered potassium hydroxide were added and the mixture was refluxed for 30 minutes. The tertiary butyl alcohol was then removed under vacuum and additional water introduced. The water layer was extracted 3 times with ether and the aqueous alkaline layer was then neutralized with hydrochloric acid. A second extraction of the aqueous layer was carried out using three 75 ml. portions of ether. The second ether extract was dried with anhydrous magnesium sulfate and the ether stripped off. The residue contained 0.64 g. of pivalic (trimethyl acetic) acid.

EXAMPLE 4

0.010 moles of cyclohexyl acetone in 10 ml. of carbon tetrachloride was added dropwise to a stirred refluxing mixture of 10 ml. carbon tetrachloride, 10 ml. tertiary butyl alcohol, and 4 g. of powdered potassium hydroxide, over a period of 8 hours. The product, 0.86 g., was isolated in the manner described in Example 1 and identified as $\alpha$-cyclohexyl propionic acid.

EXAMPLE 5

0.010 moles of benzyl alcohol was added to 4 g. of powdered anhydrous potassium hydroxide and 15 ml. of carbon tetrachloride. The solution was stirred and refluxed for 2 hours after which 50 ml. of water was added and the water phase washed with ether. The alkaline aqueous phase was then acidified and extracted with a second aliquot of ether. This resultant ether extract was dried with anhydrous magnesium sulfate and the ether stripped off leaving 0.72 g. of benzoic acid.

EXAMPLE 6

0.0096 moles benzhydrol benzyhydrol was added to 15 ml. of carbon tetrachloride and 4 g. of powdered anhydrous potassium hydroxide. The mixture was refluxed for 2 hours and then filtered to remove salts and potassium hydroxide. The carbon tetrachloride was stripped from the filtrate leaving a viscous oil which solidified on cooling. The product was identified as benzophenone (0.0096 moles) and had a melting point of 43° to 45°C.

EXAMPLE 7

0.010 moles of methyl isopropyl carbinol was refluxed with 4 g. of powdered potassium hydroxide in 15 ml. of carbon tetrachloride and 5 ml. of tertiary butyl alcohol. The reaction mixture was treated in accordance with the manner described in Example 3. 0.25 g. of pivalic acid were isolated.

EXAMPLE 8

A mixture of 0.001 moles of ortho-hydroxy benzyl alcohol, 5 ml. of carbon tetrachloride, 10 ml. of tertiary butyl alcohol and 0.030 moles of anhydrous potassium hydroxide were stirred under reflux for 2 hours. Excess solvent was then stripped from the reaction mixture under vacuum. Water was added to the residue which was acidified and then extracted with ether. The ether extract was washed several times with aqueous sodium bisulfite solution, then with water, followed by aqueous sodium bicarbonate solution and more water. The sodium bisulfite extract was acidified and treated with a solution of 2,4-dinitrophenylhydrazone, causing a precipitate to form. The precipitate was recovered by filtration, washed with water and dried, yielding of 0.047 g. of the 2,4-dinitrophenylhydrazone of ortho-hydroxybenzaldehyde (m.p. 248–250°C.) which corresponds to 0.019 g. of ortho-hydroxybenzaldehyde.

Acidification and ether extraction of the sodium bicarbonate extract failed to yield the corresponding acid.

EXAMPLE 9

0.86 g. of methyl isopropyl ketone was refluxed with 15 ml. carbon tetrachloride, 5 ml. of tertiary butyl alcohol and 4 g. of potassium tertiary butoxide. The reaction mixture was worked up in accordance with the method described in Example 3. Products recovered included pivalic acid (30%) and tertiary butyl pivalate (24%).

EXAMPLE 10

0.8 g. of neopentyl alcohol was dissolved in 15 ml. of carbon tetrachloride. 4 g. of powdered anhydrous potassium hydroxide were added and the mixture was refluxed for 1 hour. Pivalic acid (10%) and t-butyl pivalate (30%) were recovered in accordance with the method described in Example 3 while pivalaldehyde (20%) was recovered in the manner set forth in Example 8.

EXAMPLE 11

1 g. of acetophenone in 10 ml. of carbon tetrachloride was added dropwise over a period of about 1 hour to a stirring refluxing mixture of 20 ml. of carbon tetrachloride, 20 ml. of tertiary butyl alcohol and 10 g. powdered potassium hydroxide. The reaction mixture darkened as the acetophenone solution was added and was a deep brown when addition of the acetophenone solution was complete. Following completion of the acetophenone addition, 200 ml. of water was added to the reaction vessel and the resulting mixture was extracted 4 times with 100 ml. portions of ether. The aqueous layer was then acidified causing an orange precipitate to form. This precipitate was taken up in ether and the aqueous phase extracted several times with additional amounts of ether. The various ether fractions thus produced were combined, dried with anhydrous magnesium sulfate and concentrated under vacuum to yield about 1 g. of a colored solid. This solid was recrystallized from water providing 0.8 grams of benzoic acid having a melting point of 120° to 122° C.

EXAMPLE 12

A mixture containing 1 g. of diethylketone, 20 ml. of carbon tetrachloride, 20 ml. of tertiary butyl alcohol and 5 g. of powdered potassium hydroxide was stirred vigorously at room temperature. Heat generated by exothermic reaction rapidly increased the temperature of the mixture to the reflux temperature and the system refluxed for about 15 minutes without external heating. Stirring was continued for approximately 30 minutes after which 100 ml. of water was added to the reaction vessel and the resulting mixture was then extracted 4 times with 100 ml. portions of ether. The aqueous residue was acidified with hydrochloric acid and extracted 3 times with additional 100 ml. portions of ether. The ether extracts from the latter extraction were combined, dried over anhydrous magnesium sulfate and the ether solvent removed under vacuum, leaving 1 g. of a liquid residue of which 0.87 g. was identified as α-methylbutyric acid.

EXAMPLE 13

1 g. of isobutyrophenone was added to 15 ml. $CCl_4$, 5 ml. t-butyl alcohol and 5 g. powdered potassium hydroxide. The mixture was stirred at room temperature (25°C.) for 8 hours. The mixture was filtered to remove salt and potassium hydroxide. Analysis by nuclear magnetic resonance indicated approximately 50% yield of α-chloroisobutyrophenone.

EXAMPLE 14

0.010 moles of benzhydryl methyl carbinol was added to 4 g. of powdered potassium hydroxide and 15 ml. of carbon tetrachloride. The solution was stirred and refluxed for 2 hours after which 50 ml. of water was added and the water phase washed with ether. The alkaline aqueous phase was then acidified and extracted with the second aliquot of ether. This resultant ether extract was dried with anhydrous magnesium sulfate and the ether stripped off leaving 0.56 g. of β,β-diphenyl propionic acid.

EXAMPLE 15

0.01 moles of tertiary butyl methyl ketone was added to a mixture containing 15 ml. of carbon tetrachloride, 15 ml. tertiary butyl alcohol and 4 g. of powdered potassium hydroxide. The resulting mixture was stirred vigorously on a steam bath for 1½ hours. The reaction mixture was then cooled, diluted with water, and extracted with 3 aliquots of ether. The extracted aqueous layer was acidified and again extracted with 3 additional aliquots of ether. The ether extracts were combined, dried with anhydrous magnesium sulfate and the ether solvent stripped off leaving 0.80 g. of pivalic acid.

In view of the above, it will be seen that the several objects of the invention are achieved and other advantageous results attained.

As various changes could be made in the above methods without departing from the scope of the invention, it is intended that all matter contained in the above description shall be interpreted as illustrative and not in a limiting sense.

We claim:

1. A process for preparing carboxylic acids and esters from α-methyl ketones or ketones having α and α' hydrogens which comprises the steps of:

reacting a substrate selected from the group consisting of α-methyl ketones and ketones having α and α' hydrogens with a carbon tetrahalide represented by the formula $CBr_mCl_nF_p$, where $m$ and $n$ are integers between 0 and 4 inclusive, $p$ is an integer between 0 and 2 inclusive and $m+n+p=4$, in the presence of a strong base selected from the group consisting of an alkali metal hydroxide, an alkali metal alkoxide, and aluminum alkoxide to form a halogenated intermediate and a dihalocarbene;

reacting said halogenated intermediate with the base; and separating the carboxylic acid or ester product from the reaction mixture.

2. The process set forth in claim 1 wherein a solvent for the substrate and the carbon tetrahalide is also present.

3. The process set forth in claim 1 wherein the carbon tetrahalide is carbon tetrachloride.

4. The process set forth in claim 1 wherein a small proportion of water is also present during the reaction.

5. The process set forth in claim 1 wherein said strong base is potassium hydroxide.

6. The process set forth in claim 1 wherein the substrate is reacted with carbon tetrahalide at a temperature of between the solidification point of the reaction mixture and about 250°C.

7. The process set forth in claim 6 wherein the substrate is reacted with carbon tetrahalide at room temperature.

8. The process set forth in claim 6 wherein the substrate is reacted with carbon tetrahalide at atmospheric reflux temperature.

9. The process set forth in claim 6 wherein the substrate is reacted with carbon tetrahalide at a temperature of about 150°C.

10. The process set forth in claim 1 wherein an alkali metal alkoxide is present and an ester is produced.

11. The process set forth in claim 1 wherein the product is an acid and said product is separated from the reaction mixture by:

adding water to the reaction mixture to form an aqueous alkaline solution;

mixing a first aliquot of a water-immiscible organic solvent with the alkaline solution;

separating said organic solvent from the alkaline solution;

acidifying the alkaline solution;

extracting the product from the acidified solution with a second aliquot of a water-immiscible organic solvent; and recovering the product from the extract.

12. A process as set forth in claim 1 wherein the substrate is an α-methyl ketone.

13. The process set forth in claim 12 wherein benzoic acid is prepared from acetophenone.

14. The process set forth in claim 12 wherein pivalic acid is prepared from t-butyl methyl ketone.

15. A process for preparing carboxylic acids and esters from ketones having the structural formula:

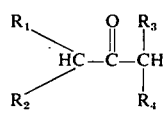

where $R_1$, $R_2$, $R_3$ and $R_4$ are selected from the group consisting of hydrogen, alkyl, phenyl, alkynyl, alkenyl, cycloalkyl and cycloalkenyl, and the product is a compound represented by the general formula:

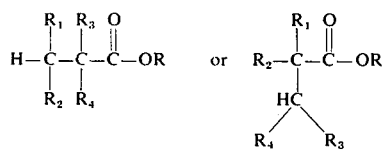

where $R_1$, $R_2$, $R_3$ and $R_4$ are as defined above and R is H or alkyl, the process comprising the steps of:

reacting said ketone with a carbon tetrahalide represented by the formula $CBr_mCl_nF_p$ where $m$ and $n$ are integers between 0 and 4 inclusive, $p$ is an integer between 0 and 2 inclusive, and $m+n+p=4$, in the presence of a strong base selected from the group consisting of an alkali metal hydroxide, an alkali metal alkoxide and an aluminum alkoxide to form a halogenated intermediate and a dihalocarbene;

reacting said halogenated intermediate with the base; and separating the carboxylic acid or ester product from the reaction mixture.

16. A process as set forth in claim 15 wherein the initial reaction is carried out at a temperature between a solidification point of the reaction mixture and about 250°C.

17. The process set forth in claim 15 wherein trimethyl acetic acid is prepared from methyl isopropyl ketone.

18. A process as set forth in claim 17 wherein the initial reaction is carried out at a temperature between the solidification point of the reaction mixture and about 250°C.

19. The process set forth in claim 15 wherein β,β-diphenylpropionic acid is prepared from 1,1-diphenyl acetone.

20. The process set forth in claim 15 wherein α-cyclohexylpropionic acid is prepared from cyclohexyl acetone.

21. The process set forth in claim 15 wherein α-butyric acid is prepared from diethyl ketone.

22. A process for preparing carboxylic acids and esters from a ketone having the general formula:

where at least one of X and Y is selected from the group consisting of cycloalkyl and cycloalkenyl, and the other of X and Y is selected from the group consisting of cycloalkyl, cycloalkenyl and substituents having the general formula:

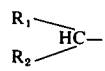

where $R_1$ and $R_2$ are selected from the group consisting of hydrogen, alkyl, phenyl, alkenyl, alkynyl, cycloalkyl and cycloalkenyl, the process comprising the steps of:

reacting said ketone with a carbon tetrahalide represented by the formula $CBr_mCl_nF_p$ where $m$ and $n$ are integers between 0 and 4 inclusive, $p$ is an integer between 0 and 2 inclusive, and $m+n+p=4$, in the presence of a strong base selected from the group consisting of an alkali metal hydroxide, an alkali metal alkoxide and an aluminum alkoxide to form a halogenated intermediate and a dihalocarbene;

reacting said halogenated intermediate with the base; and separating the carboxylic acid or ester product from the reaction mixture.

23. A process as set forth in claim 22 wherein the initial reaction is carried out at a temperature between the solidification point of the reaction mixture and about 250°C.

24. A process for preparing carboxylic acids and esters from a ketone selected from the group consisting of cyclohexanone, 3-ethyl cyclohexanone, cycloheptanone cyclohexene-4-one, 1-methyl cyclohexene-4-one, cycloheptene-4-one and 1,2 dimethyl cycloheptene-4-one, comprising the steps of:

reacting said ketone with a carbon tetrahalide represented by the formula $CBr_mCl_nF_p$ where $m$ and $n$ are integers between 0 and 4 inclusive, $p$ is an integer between 0 and 2 inclusive, and $m+n+p=4$, in the presence of a strong base selected from the group consisting of an alkali metal hydroxide, an alkali metal alkoxide and an aluminum alkoxide to form a halogenated intermediate and a dihalocarbene;

reacting said halogenated intermediate with the base; and separating the carboxylic acid or ester product from the reaction mixture.

* * * * *